(12) United States Patent
Blin et al.

(10) Patent No.: US 7,025,953 B2
(45) Date of Patent: Apr. 11, 2006

(54) NAIL POLISH COMPOSITION COMPRISING A POLYMER

(75) Inventors: Xavier Blin, Paris (FR); Véronique Ferrari, Maisons-Alfort (FR); Frédéric Auguste, Chevilly-Larue (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/046,568

(22) Filed: Jan. 16, 2002

(65) Prior Publication Data

US 2002/0192168 A1 Dec. 19, 2002

Related U.S. Application Data
(60) Provisional application No. 60/330,767, filed on Oct. 30, 2001.

(30) Foreign Application Priority Data

Jan. 17, 2001 (FR) .......................................... 01 00623

(51) Int. Cl.
*A61K 7/02* (2006.01)

(52) U.S. Cl. ....................... 424/61; 424/78.02; 424/401
(58) Field of Classification Search ................... 424/61, 424/401, 78.02, DIG. 5
See application file for complete search history.

(56) References Cited

U.S. PATENT DOCUMENTS

| 2,379,413 | A | 7/1945 | Bradley |
| 2,450,940 | A | 10/1948 | Cowan et al. |
| 2,662,068 | A | 12/1953 | Floyd |

(Continued)

FOREIGN PATENT DOCUMENTS

| CA | 2003346 | 5/1990 |
| CA | 1319306 | 6/1993 |
| DE | 38 39 136 A1 | 5/1990 |

(Continued)

OTHER PUBLICATIONS

English language abstract of JP 78/043577.
English language DERWENT abstract of WO 01/97773.
English language DERWENT abstract of WO 02/056847.
English language DERWENT abstract of WO 02/056848.
English language DERWENT abstract of WO 02/47622.
English language DERWENT abstract of WO 02/47629.
English language DERWENT abstract of WO 02/47630.
English language DERWENT abstract of WO 86/04916.
Estee Lauder MagnaScopic Maximum Volume mascara product packaging, believed to have first been sold in 2003.
Estee Lauder's Response to Plaintiff's First Set of Interrogatories (Nos. 1–6), dated Sep. 27, 2004, in the on–going litigation L'Oreal S.A., et al. v. The Estee Lauder Companies Inc., et al., Civil Action No. 04–1660 (D.N.J.).

McCutcheon's vol. 1: Emulsifiers & Detergents, North American Edition MC Publishing Co., Glen Rock NJ (1993), pp. 272–273.
Origins Full Story™ Lush lash mascara product packaging, believed to have first been sold in 2003.
English language DERWENT abstract of DE 42 08 297.
English language DERWENT abstract of DE 195 43 988.
English language DERWENT abstract of DE 199 51 010.
English language DERWENT abstract of DE 38 43 892.
English language DERWENT abstract of DE 42 34 886.
English language DERWENT abstract of EP 0 169 997 B.
English language DERWENT abstract of 0 749 748.
English language DERWENT abstract of FR 2 796 272.
English language DERWENT abstract of FR 2 296 273.
English language DERWENT abstract of FR 2 804 017.
English language DERWENT abstract of FR 2 804 018.
English language DERWENT abstract of FR 2 810 562.
English language DERWENT abstract of FR 2 811 225.
English language DERWENT abstract of FR 2 817 739.
English language DERWENT abstract of FR 2 817 740.
English language DERWENT abstract of FR 2 817 743.
English language DERWENT abstract of FR 2 819 399.
English language DERWENT abstract of FR 2 819 400.
English language DERWENT abstract of JP 10/120903.
English language DERWENT abstract of JP 11/335228.
English language DERWENT abstract of JP 11/335242.
English language DERWENT abstract of JP 11/335254.
English language DERWENT abstract of JP 2000038314 A.
English language DERWENT abstract of JP 2000038316 A and JP 2000038316 A.
English language DERWENT abstract of JP 2000038321 A.
English language DERWENT abstract of JP 2000086427 A.
English language DERWENT abstract of JP 2000086429 A.
English language DERWENT abstract of JP 2000086438 A.
English language DERWENT abstract of JP 9/20631.
Handbook of Cosmetic Science and Tech. Elsevier Advanced Tech., 1st Edition (1994), p. 19.
International Search Report in PCT/FR01/03726, dated Apr. 18, 2002.
Kirk–Othmer,"Encyclopedia of Chemical Technology", Third Edition, vol. 22, John Wiley & Sons, 1983, pp. 332–342.

(Continued)

*Primary Examiner*—Jyothsna Venkat
(74) *Attorney, Agent, or Firm*—Finnegan, Henderson, Farabow, Garrett & Dunner, L.L.P.

(57) ABSTRACT

The invention relates to a nail polish composition comprising at least one liquid organic phase comprising at least one volatile organic solvent, the liquid organic phase being structured by at least one polymer with a weight-average molecular mass of less than or equal to 100 000 comprising a) a polymer backbone having hydrocarbonaceous repeat units which are provided with at least one heteroatom and optionally b) optionally functionalized pendent and/or end fatty chains which have from 6 to 120 carbon atoms and which are bonded to these units. This composition is provided in particular in the form of a nail polish stick.

17 Claims, No Drawings

U.S. PATENT DOCUMENTS

| | | |
|---|---|---|
| 2,663,649 A | 12/1953 | Winkler |
| 2,890,097 A | 6/1959 | Coe |
| 2,962,461 A | 11/1960 | Toussaint et al. |
| 3,086,914 A | 4/1963 | Soloway ............... 167/85 |
| 3,141,787 A | 7/1964 | Goetze et al. |
| 3,148,125 A | 9/1964 | Strianse et al. |
| 3,156,572 A | 11/1964 | Carlick et al. |
| 3,255,082 A | 6/1966 | Barton |
| 3,341,465 A | 9/1967 | Kaufman et al. |
| 3,412,115 A | 11/1968 | Floyd et al. |
| 3,615,289 A | 10/1971 | Felton |
| 3,645,705 A | 2/1972 | Miller et al. |
| 3,778,394 A | 12/1973 | Lovald et al. |
| 3,819,342 A | 6/1974 | Gunderman et al. |
| 3,857,960 A | 12/1974 | Mackles |
| 3,926,655 A | 12/1975 | Miles |
| 3,937,811 A | 2/1976 | Papantoniou et al. |
| 3,969,087 A | 7/1976 | Saito et al. |
| 4,049,792 A | 9/1977 | Elsnau |
| 4,051,159 A | 9/1977 | Tsoucalas et al. |
| 4,062,819 A | 12/1977 | Mains et al. |
| RE29,871 E | 12/1978 | Papantoniou et al. |
| 4,128,436 A | 12/1978 | O'Hara et al. |
| 4,137,306 A | 1/1979 | Rubino et al. |
| 4,148,875 A | 4/1979 | Barnett et al. |
| 4,150,002 A | 4/1979 | Drawert et al. |
| 4,275,054 A | 6/1981 | Sebag et al. |
| 4,275,055 A | 6/1981 | Nachtigal et al. ............ 424/70 |
| 4,278,658 A | 7/1981 | Hooper et al. |
| 4,279,658 A | 7/1981 | Harvey et al. |
| 4,337,298 A | 6/1982 | Karim et al. |
| 4,341,671 A | 7/1982 | Bolze et al. |
| 4,376,194 A | 3/1983 | Tanaka et al. |
| 4,387,090 A | 6/1983 | Bolich, Jr. ............... 424/70 |
| 4,438,240 A | 3/1984 | Tanaka et al. |
| 4,466,936 A | 8/1984 | Schapel |
| 4,536,405 A | 8/1985 | Nara et al. |
| 4,552,693 A | 11/1985 | Hussain et al. ............ 252/522 |
| 4,571,267 A | 2/1986 | Drawert et al. |
| 4,620,492 A | 11/1986 | Vogg et al. |
| 4,655,836 A | 4/1987 | Drawert et al. |
| 4,663,428 A | 5/1987 | Okitu et al. |
| 4,699,779 A | 10/1987 | Palinczar |
| 4,712,571 A | 12/1987 | Remz et al. |
| 4,769,285 A | 9/1988 | Rasmussen |
| 4,806,338 A | 2/1989 | Smith ..................... 424/47 |
| 4,806,345 A | 2/1989 | Bhattacharyya ............. 424/70 |
| 4,820,765 A | 4/1989 | Whyzmuzis |
| 4,822,601 A | 4/1989 | Goode et al. |
| 4,871,536 A | 10/1989 | Arraudeau et al. ......... 424/59 |
| 4,937,069 A | 6/1990 | Shin |
| 4,952,245 A | 8/1990 | Iwano et al. |
| 5,034,219 A | 7/1991 | Deshpande et al. |
| 5,061,289 A | 10/1991 | Clausen et al. |
| 5,069,897 A | 12/1991 | Orr ........................ 424/66 |
| 5,073,364 A | 12/1991 | Giezendanner et al. |
| 5,085,859 A | 2/1992 | Halloran et al. |
| 5,102,656 A | 4/1992 | Kasat |
| 5,186,318 A | 2/1993 | Oestreich et al. ........... 206/37 |
| 5,196,260 A | 3/1993 | Dirshl et al. |
| 5,223,559 A | 6/1993 | Arraudeau et al. |
| 5,268,029 A | 12/1993 | Demangeon et al. |
| 5,272,241 A | 12/1993 | Lucarelli et al. |
| 5,290,555 A | 3/1994 | Guthauser et al. |
| 5,302,398 A | 4/1994 | Egidio et al. |
| 5,342,894 A | 8/1994 | Robeson et al. |
| 5,362,482 A | 11/1994 | Yoneyama et al. |
| 5,372,852 A | 12/1994 | Titterington et al. |
| 5,389,363 A | 2/1995 | Snyder et al. |
| 5,472,686 A | 12/1995 | Tsubaki et al. |
| 5,486,431 A | 1/1996 | Tuttle et al. |
| 5,489,431 A | 2/1996 | Ascione et al. |
| 5,500,209 A | 3/1996 | Mendolia et al. |
| 5,505,937 A | 4/1996 | Castrogiovanni et al. |
| 5,510,452 A | 4/1996 | Santhanam |
| 5,536,871 A | 7/1996 | Santhanam |
| 5,538,718 A | 7/1996 | Aul et al. |
| 5,538,793 A | 7/1996 | Inokuchi et al. |
| 5,540,853 A | 7/1996 | Trinh et al. |
| 5,603,925 A | 2/1997 | Ross et al. |
| 5,605,651 A | 2/1997 | Balzer |
| 5,610,199 A | 3/1997 | Cohen et al. |
| 5,612,043 A | 3/1997 | Deprez et al. |
| 5,616,331 A | 4/1997 | Allard et al. |
| 5,618,523 A | 4/1997 | Zysman et al. |
| 5,620,693 A | 4/1997 | Piot et al. |
| 5,645,632 A | 7/1997 | Pavlin |
| 5,667,770 A | 9/1997 | Szweda et al. |
| 5,679,357 A | 10/1997 | Dubief et al. |
| 5,683,817 A | 11/1997 | Kenmochi |
| 5,702,519 A | 12/1997 | Nitta et al. |
| 5,719,255 A | 2/1998 | Heucher et al. |
| 5,747,625 A | 5/1998 | Furukawa et al. |
| 5,750,125 A | 5/1998 | Lahanas et al. |
| 5,750,127 A | 5/1998 | Rokitowski |
| 5,750,489 A | 5/1998 | Garcia et al. |
| 5,769,902 A | 6/1998 | Samain |
| 5,780,517 A | 7/1998 | Cohen et al. |
| 5,783,657 A | 7/1998 | Pavlin et al. |
| 5,800,816 A | 9/1998 | Brieva et al. ................. 424/63 |
| 5,807,968 A | 9/1998 | Heinrich et al. |
| 5,830,444 A | 11/1998 | Miguel |
| 5,830,483 A | 11/1998 | Seidel et al. |
| 5,837,223 A | 11/1998 | Barone et al. |
| 5,849,275 A | 12/1998 | Calello et al. |
| 5,849,278 A | 12/1998 | Piot et al. |
| 5,849,333 A | 12/1998 | Nordhauser et al. |
| 5,851,517 A | 12/1998 | Mougin et al. |
| 5,857,903 A | 1/1999 | Ramspeck et al. |
| 5,858,338 A | 1/1999 | Piot et al. |
| 5,866,149 A | 2/1999 | Piot et al. |
| 5,871,764 A | 2/1999 | Diaz et al. |
| 5,874,069 A | 2/1999 | Mendolia et al. ............. 424/65 |
| 5,882,363 A | 3/1999 | Spaulding et al. |
| 5,891,424 A | 4/1999 | Bretzler et al. |
| 5,897,869 A | 4/1999 | Roulier et al. ............. 424/401 |
| 5,902,592 A | 5/1999 | Bara et al. |
| 5,908,631 A | 6/1999 | Arnaud et al. |
| 5,911,974 A | 6/1999 | Brieva et al. ................. 424/64 |
| 5,919,441 A | 7/1999 | Mendolia et al. ......... 424/78.08 |
| 5,925,337 A | 7/1999 | Arraudeau et al. |
| 5,945,095 A | 8/1999 | Mougin et al. |
| 5,945,112 A | 8/1999 | Flynn et al. |
| 5,959,009 A | 9/1999 | Konik et al. ................. 524/261 |
| 5,961,998 A | 10/1999 | Arnaud et al. |
| 5,965,112 A | 10/1999 | Brieva et al. ................. 424/64 |
| 5,972,095 A * | 10/1999 | Graves et al. ......... 106/287.11 |
| 5,972,354 A | 10/1999 | de la Poterie et al. |
| 5,972,359 A | 10/1999 | Sine et al. |
| 5,976,514 A | 11/1999 | Guskey et al. |
| 5,981,680 A | 11/1999 | Petroff et al. |
| 5,985,298 A | 11/1999 | Brieva et al. |
| 5,993,787 A | 11/1999 | Sun et al. |
| 5,998,570 A | 12/1999 | Pavlin et al. |
| 6,001,980 A | 12/1999 | Borzo et al. |
| 6,004,567 A | 12/1999 | Marchi-Lemann et al. |
| 6,007,799 A | 12/1999 | Lee et al. |
| 6,019,962 A | 2/2000 | Rabe et al. |
| 6,036,947 A | 3/2000 | Barone et al. |
| 6,045,782 A | 4/2000 | Krog et al. |
| 6,045,823 A | 4/2000 | Vollhardt et al. |

| Patent No. | Date | Name | | Pub. No. | Date | Name |
|---|---|---|---|---|---|---|
| 6,051,216 A | 4/2000 | Barr et al. ............... 424/78.35 | | 2002/0119171 A1 | 8/2002 | Gruning et al. |
| 6,054,517 A | 4/2000 | Spaulding et al. | | 2002/0120036 A1 | 8/2002 | Pinzon et al. |
| 6,060,072 A | 5/2000 | Konik et al. ............... 424/401 | | 2002/0122781 A1 | 9/2002 | Pinzon et al. |
| 6,063,398 A | 5/2000 | Gueret | | 2002/0131947 A1 | 9/2002 | Nakanishi |
| 6,066,328 A | 5/2000 | Ribier et al. | | 2002/0141958 A1 | 10/2002 | Maio et al. |
| 6,074,654 A | 6/2000 | Drechsler et al. ........... 424/401 | | 2002/0150602 A1 | 10/2002 | Livoreil et al. |
| 6,103,249 A | 8/2000 | Roulier et al. .............. 424/401 | | 2002/0159964 A1 | 10/2002 | Nakanishi et al. |
| 6,106,820 A | 8/2000 | Morrissey et al. | | 2002/0168335 A1 | 11/2002 | Collin |
| 6,111,055 A | 8/2000 | Berger et al. | | 2002/0172696 A1 | 11/2002 | Ferrari |
| 6,156,325 A | 12/2000 | Farer et al. ................. 424/401 | | 2002/0189030 A1 | 12/2002 | Collin |
| 6,156,804 A | 12/2000 | Chevalier et al. | | 2002/0192168 A1 | 12/2002 | Blin et al. |
| 6,165,454 A | 12/2000 | Patel et al. | | 2003/0012764 A1 | 1/2003 | Collin |
| 6,165,971 A | 12/2000 | Oppenlander et al. | | 2003/0026772 A1 | 2/2003 | Jager-Lezer et al. |
| 6,171,347 B1 | 1/2001 | Kunz | | 2003/0044367 A1 | 3/2003 | Simon et al. |
| 6,177,523 B1 | 1/2001 | Reich et al. ................. 525/459 | | 2003/0086883 A1 | 5/2003 | Feng et al. |
| 6,180,117 B1 | 1/2001 | Berthiaume et al. | | 2003/0147837 A1 | 8/2003 | Cavazzuti et al. |
| 6,180,123 B1 | 1/2001 | Mondet | | 2003/0161807 A1 | 8/2003 | Lemann |
| 6,190,673 B1 | 2/2001 | Guskey et al. .............. 424/401 | | 2003/0161848 A1 | 8/2003 | Ferrari et al. |
| 6,197,100 B1 | 3/2001 | Melbouci | | 2003/0185780 A1 | 10/2003 | Ferrari et al. |
| 6,203,780 B1 | 3/2001 | Arnaud et al. | | 2003/0198613 A1 | 10/2003 | Feng et al. |
| 6,203,807 B1 | 3/2001 | Lemann | | 2004/0013625 A1 | 1/2004 | Kanji |
| 6,214,326 B1 | 4/2001 | Dupuis | | 2004/0028636 A1 | 2/2004 | Collin |
| 6,214,329 B1 | 4/2001 | Brieva et al. | | 2004/0042980 A1 | 3/2004 | Kanji et al. |
| 6,221,389 B1 | 4/2001 | Cannell et al. | | 2004/0086478 A1 | 5/2004 | Ferrari |
| 6,224,851 B1 | 5/2001 | Bara | | 2004/0091510 A1 | 5/2004 | Feng et al. |
| 6,242,509 B1 | 6/2001 | Berger et al. | | 2004/0126401 A1 | 7/2004 | Collin |
| 6,251,375 B1 | 6/2001 | Bara | | 2004/0166076 A1 | 8/2004 | Ferrari et al. |
| 6,251,409 B1 | 6/2001 | Hegyi et al. | | 2004/0166133 A1 | 8/2004 | Cavazzuti et al. |
| 6,254,876 B1 | 7/2001 | de la Poterie et al. | | | | |
| 6,254,877 B1 | 7/2001 | De La Poterie et al. | | FOREIGN PATENT DOCUMENTS | | |
| 6,264,933 B1 | 7/2001 | Bodelin et al. | | DE | 38 43 892 A1 | 6/1990 |
| 6,268,466 B1 | 7/2001 | MacQueen et al. | | DE | 42 08 297 A1 | 9/1993 |
| 6,280,846 B1 | 8/2001 | Darby et al. | | DE | 42 34 886 A1 | 4/1994 |
| 6,287,552 B1 | 9/2001 | Tournilhac et al. | | DE | 195 43 988 A1 | 5/1997 |
| 6,325,994 B1 | 12/2001 | Collin et al. | | DE | 197 07 309 A1 | 8/1998 |
| 6,348,563 B1 | 2/2002 | Fukuda et al. | | DE | 197 50 246 A1 | 5/1999 |
| 6,372,235 B1 | 4/2002 | Livoreil et al. | | DE | 199 51 010 A1 | 4/2001 |
| 6,376,078 B1 | 4/2002 | Inokuchi | | EP | 0 169 997 B1 | 2/1986 |
| 6,383,502 B1 | 5/2002 | Dunshee et al. | | EP | 0 370 470 B1 | 5/1990 |
| 6,399,080 B1 | 6/2002 | Bara | | EP | 0 374 332 A1 | 6/1990 |
| 6,399,081 B1 | 6/2002 | Nakanishi et al. | | EP | 0 444 633 A2 | 9/1991 |
| 6,402,408 B1 * | 6/2002 | Ferrari ........................ 401/64 | | EP | 0 295 886 B1 | 1/1992 |
| 6,423,306 B1 | 7/2002 | Caes et al. | | EP | 0 557 196 A1 | 8/1993 |
| 6,423,324 B1 | 7/2002 | Murphy et al. | | EP | 0 602 905 B1 | 6/1994 |
| 6,428,773 B1 | 8/2002 | Oko et al. | | EP | 0 609 132 B1 | 8/1994 |
| 6,432,391 B1 | 8/2002 | Bara | | EP | 0 623 670 A2 | 11/1994 |
| 6,447,759 B1 | 9/2002 | Noguchi et al. | | EP | 0 628 582 B1 | 12/1994 |
| 6,469,131 B1 | 10/2002 | Lawson et al. | | EP | 0 412 710 B1 | 7/1995 |
| 6,475,500 B1 | 11/2002 | Vatter et al. | | EP | 0 673 642 B1 | 9/1995 |
| 6,479,686 B1 | 11/2002 | Nakanishi et al. | | EP | 0 708 114 A1 | 4/1996 |
| 6,482,400 B1 | 11/2002 | Collin | | EP | 0 749 746 A1 | 12/1996 |
| 6,491,931 B1 | 12/2002 | Collin | | EP | 0 749 747 A1 | 12/1996 |
| 6,497,861 B1 | 12/2002 | Wang et al. | | EP | 0 749 748 A1 | 12/1996 |
| 6,506,716 B1 | 1/2003 | Delplancke et al. | | EP | 0 775 483 A1 | 5/1997 |
| 6,649,173 B1 | 11/2003 | Arnaud et al. | | EP | 0 797 976 A2 | 10/1997 |
| 6,682,748 B1 | 1/2004 | De La Poterie et al. | | EP | 0 820 764 A1 | 1/1998 |
| 6,726,917 B1 | 4/2004 | Kanji | | EP | 0 847 752 A1 | 6/1998 |
| 6,761,881 B1 | 7/2004 | Bara | | EP | 0 877 063 B1 | 11/1998 |
| 6,875,245 B1 | 4/2005 | Pavlin | | EP | 0 879 592 A2 | 11/1998 |
| 2001/0014312 A1 | 8/2001 | Nakanishi et al. | | EP | 0 887 073 A1 | 12/1998 |
| 2001/0028887 A1 | 10/2001 | Duin et al. | | EP | 0 923 928 A1 | 6/1999 |
| 2001/0031280 A1 | 10/2001 | Ferrari et al. | | EP | 0 925 780 A1 | 6/1999 |
| 2001/0033846 A1 | 10/2001 | Roulier et al. | | EP | 0 928 608 A2 | 7/1999 |
| 2002/0044918 A1 | 4/2002 | Bara | | EP | 0 930 058 B1 | 7/1999 |
| 2002/0058053 A1 | 5/2002 | Nakanishi et al. | | EP | 0 930 060 A1 | 7/1999 |
| 2002/0081323 A1 | 6/2002 | Nakanish et al. | | EP | 0 943 340 A1 | 9/1999 |
| 2002/0102225 A1 | 8/2002 | Hess et al. | | EP | 0 958 804 A2 | 11/1999 |
| 2002/0107314 A1 | 8/2002 | Pinzon et al. | | EP | 0 958 805 A2 | 11/1999 |
| 2002/0111330 A1 | 8/2002 | Pinzon et al. | | EP | 0 958 811 A1 | 11/1999 |
| 2002/0114771 A1 | 8/2002 | Nakanishi | | EP | 0 959 066 A2 | 11/1999 |
| 2002/0114773 A1 | 8/2002 | Kanji et al. | | EP | 0 959 091 A1 | 11/1999 |

| | | | | | | |
|---|---|---|---|---|---|---|
| EP | 0 976 390 A1 | 2/2000 | | JP | 10/007527 | 1/1998 |
| EP | 0 984 025 A2 | 3/2000 | | JP | 10/120903 | 5/1998 |
| EP | 1 002 514 A1 | 5/2000 | | JP | 10/212213 | 8/1998 |
| EP | 1 031 342 A1 | 8/2000 | | JP | 10/259344 | 9/1998 |
| EP | 1 048 282 A1 | 11/2000 | | JP | 11/106216 | 4/1999 |
| EP | 1 053 742 A1 | 11/2000 | | JP | 11/335228 | 12/1999 |
| EP | 1 062 944 A1 | 12/2000 | | JP | 11/335242 | 12/1999 |
| EP | 1 062 959 A1 | 12/2000 | | JP | 11/335254 | 12/1999 |
| EP | 1 064 919 A1 | 1/2001 | | JP | 2000038314 A | 2/2000 |
| EP | 1 064 920 A1 | 1/2001 | | JP | 2000038316 A | 2/2000 |
| EP | 1 066 814 A1 | 1/2001 | | JP | 2000038317 A | 2/2000 |
| EP | 1 068 854 A1 | 1/2001 | | JP | 2000038321 A | 2/2000 |
| EP | 1 068 855 A1 | 1/2001 | | JP | 2000086427 A | 2/2000 |
| EP | 1 068 856 A1 | 1/2001 | | JP | 2000086429 A | 3/2000 |
| EP | 1 086 945 A1 | 3/2001 | | JP | 2000086438 A | 3/2000 |
| EP | 1 090 627 B1 | 4/2001 | | WO | WO 86/04916 | 8/1986 |
| EP | 1 095 959 A2 | 5/2001 | | WO | WO 87/03783 | 7/1987 |
| EP | 1 114 636 A1 | 7/2001 | | WO | WO 91/12793 | 9/1991 |
| EP | 1 213 011 A1 | 6/2002 | | WO | WO 93/21763 | 11/1993 |
| EP | 1 213 316 A2 | 6/2002 | | WO | WO 93/23008 | 11/1993 |
| FR | 1 529 329 | 5/1968 | | WO | WO 94/18261 | 8/1994 |
| FR | 2 232 303 | 1/1975 | | WO | WO 94/21233 | 9/1994 |
| FR | 2 674 126 | 9/1992 | | WO | WO 95/15741 | 6/1995 |
| FR | 2 785 179 | 5/2000 | | WO | WO 95/24887 | 9/1995 |
| FR | 2 796 270 | 1/2001 | | WO | WO 95/33000 | 12/1995 |
| FR | 2 796 271 | 1/2001 | | WO | WO 96/15761 | 5/1996 |
| FR | 2 796 272 | 1/2001 | | WO | WO 96/40044 | 12/1996 |
| FR | 2 796 273 | 1/2001 | | WO | WO 97/17057 | 5/1997 |
| FR | 2 796 276 | 1/2001 | | WO | WO 97/36573 | 10/1997 |
| FR | 2 802 806 | 6/2001 | | WO | WO 98/17243 | 4/1998 |
| FR | 2 804 017 | 7/2001 | | WO | WO 98/17705 | 4/1998 |
| FR | 2 804 018 | 7/2001 | | WO | WO 98/22078 | 5/1998 |
| FR | 2 810 562 | 12/2001 | | WO | WO 98/27162 | 6/1998 |
| FR | 2 811 225 | 1/2002 | | WO | WO 98/42298 | 10/1998 |
| FR | 2 811 552 | 1/2002 | | WO | WO 98/47470 | 10/1998 |
| FR | 2 816 506 | 5/2002 | | WO | WO 98/52534 | 11/1998 |
| FR | 2 817 739 | 6/2002 | | WO | WO 98/58623 | 12/1998 |
| FR | 2 817 740 | 6/2002 | | WO | WO 99/24002 | 5/1999 |
| FR | 2 817 743 | 6/2002 | | WO | WO 00/27350 | 5/2000 |
| FR | 2 819 399 | 7/2002 | | WO | WO 00/40216 | 7/2000 |
| FR | 2 819 400 | 7/2002 | | WO | WO 00/61080 | 10/2000 |
| FR | 2 819 402 | 7/2002 | | WO | WO 00/61081 | 10/2000 |
| GB | 1 117 129 | 6/1968 | | WO | WO 00/74519 A2 | 12/2000 |
| GB | 1 194 901 | 6/1970 | | WO | WO 01/51020 A1 | 7/2001 |
| GB | 1 194 902 | 6/1970 | | WO | WO 01/52799 A1 | 7/2001 |
| GB | 1 220 069 | 1/1971 | | WO | WO 01/97758 A2 | 12/2001 |
| GB | 1 273 004 | 5/1972 | | WO | WO 01/97773 A1 | 12/2001 |
| GB | 1 444 204 | 7/1976 | | WO | WO 02/03932 A2 | 1/2002 |
| GB | 2 014 852 | 9/1979 | | WO | WO 02/03935 A2 | 1/2002 |
| GB | 2 021 411 A | 12/1979 | | WO | WO 02/03950 A2 | 1/2002 |
| GB | 2 021 411 | 12/1979 | | WO | WO 02/03951 A2 | 1/2002 |
| GB | 2 147 305 A | 5/1985 | | WO | WO 02/47605 A2 | 6/2002 |
| GB | 2 196 978 A | 5/1988 | | WO | WO 02/47608 A2 | 6/2002 |
| GB | 2 196 978 | 5/1988 | | WO | WO 02/47619 A2 | 6/2002 |
| JP | 50/58242 | 5/1975 | | WO | WO 02/47620 A2 | 6/2002 |
| JP | 53/043577 | 4/1978 | | WO | WO 02/47622 A2 | 6/2002 |
| JP | 56/123909 | 9/1981 | | WO | WO 02/47627 A2 | 6/2002 |
| JP | 56/166276 | 12/1981 | | WO | WO 02/47629 A1 | 6/2002 |
| JP | 61/065809 | 4/1986 | | WO | WO 02/47630 A1 | 6/2002 |
| JP | 62/061911 | 3/1987 | | WO | WO 02/47658 A2 | 6/2002 |
| JP | 2/127568 | 5/1990 | | WO | WO 02/49583 A1 | 6/2002 |
| JP | 02/200612 | 8/1990 | | WO | WO 02/49601 A1 | 6/2002 |
| JP | 2/216279 | 8/1990 | | WO | WO 02/055030 A2 | 7/2002 |
| JP | 3/014683 | 1/1991 | | WO | WO 02/055031 A2 | 7/2002 |
| JP | 04/346909 | 12/1992 | | WO | WO 02/056845 A1 | 7/2002 |
| JP | 7/179795 | 7/1995 | | WO | WO 02/056847 A1 | 7/2002 |
| JP | 7/267827 | 10/1995 | | WO | WO 02/056848 A1 | 7/2002 |
| JP | 8/225316 | 9/1996 | | WO | WO 02/092047 A1 | 11/2002 |
| JP | 9/20631 | 1/1997 | | WO | WO 02/092663 A1 | 11/2002 |
| JP | 09/255560 | 9/1997 | | WO | WO 02/102322 A2 | 12/2002 |
| JP | 9/295922 | 11/1997 | | | | |

OTHER PUBLICATIONS

English language DERWENT abstract of JP A 62061911.
English language DERWENT abstract of JP 02/200612.
English language DERWENT abstract of JP 09/255560.
English language DERWENT abstract of JP 10/007527.
English language DERWENT abstract of EP 0 820 764 A1.
English language DERWENT abstract of JP 10/212213.
English language DERWENT abstract of EP 0 923 928 A1.
English language DERWENT abstract of EP 0 925 780 A1.
English language DERWENT abstract of EP 0 943 340 A1.
English language DERWENT abstract of EP 1 068 856 A1.
English language DERWENT abstract of FR 2 796 270.
English language DERWENT abstract of FR 2 796 271.
English language DERWENT abstract of FR 2 796 276.
English language DERWENT abstract of FR 2 811 552 A1.
English language DERWENT abstract of FR 2 816 506.
English language DERWENT abstract of FR 2 232 303.
English language DERWENT abstract of JP 53043577.
English language DERWENT abstract of JP 56123909.
English language DERWENT abstract of JP 61065809.
English language DERWENT abstract of FR 2 674 126.
English language DERWENT abstract of JP 04346909.
English language DERWENT abstract of EP 0 557 196 A1.
English language DERWENT abstract of EP 0 609 132.
English language DERWENT abstract of JP 7267827.
English language DERWENT abstract of JP 8225316.
English language DERWENT abstract of EP 0 749 746 A1.
English language DERWENT abstract of EP 0 749 747 A1.
English language DERWENT abstract of EP 0 775 483 A1.
English language DERWENT abstract of EP 0 847 752 A1.
English language DERWENT abstract of EP 0 879 592 A2.
English language DERWENT abstract of EP 0 887 073 A1.
English language DERWENT abstract of JP 11106216.
English language DERWENT abstract of EP 0 959 066 A2.
English language DERWENT abstract of EP 0 930 058 B1.
English language DERWENT abstract of EP 0 930 060 A1.
English language DERWENT abstract of EP 0 958 811 A1.
English language DERWENT abstract of EP 0 959 091 A1.
English language DERWENT abstract of EP 0 976 390 A1.
English language DERWENT abstract of EP 0 984 025 A2.
English language DERWENT abstract of FR 2 785 179.
English language DERWENT abstract of EP 1 002 514.
English language DERWENT abstract of EP 1 031 342 A1.
English language DERWENT abstract of EP 1 048 282 A1.
English language DERWENT abstract of EP 1 053 742.
English language DERWENT abstract of EP 1 064 919.
English language DERWENT abstract of EP 1 064 920.
English language DERWENT abstract of EP 1 066 814.
English language DERWENT abstract of EP 1 088 854 A1.
English language DERWENT abstract of EP 1 068 855 A1.
English language DERWENT abstract of EP 1 086 945 A1.
English language DERWENT abstract of EP 1 090 627 B1.
English language DERWENT abstract of FR 2 802 806.
English language DERWENT abstract of EP 1 114 636 A1.
English language DERWENT abstract of WO 02/055031 A1.
English language DERWENT abstract of FR 2 819 402.
English language DERWENT abstract of WO 02/056845 A1.
English language DERWENT abstract of JP 9295922 A.
English language DERWENT abstract of JP 7179795A.
English language DERWENT abstract of JP 3014683.
English language DERWENT abstract of JP 2216279.
English language DERWENT abstract of JP 2127568.
English language DERWENT abstract of JP 10259344.
English language DERWENT abstract of DE 3839136.
English language DERWENT abstract of DE 197 07 309.
English language DERWENT abstract of DE 197 50 246.
English language DERWENT abstract of JP 56166276A.
Certified English translation of FR 1 529 329.
Milan Jokić et al., *A Novel Type of Small Organic Gelators: Bis(Amino Acid) Oxalyl Amides*, 1995 J. Chem. Soc., Chem. Commun., 1723–1724.
Yasuda et al., *Novel low–molecular–weight Organic Gels: N,N', N"–Tristearyltrimesamide/Organic Solvent System,"* Chemistry Letters, pp. 575–576, 1996, the month of publication is not available.
Kenji Hanabusa et al., *Prominent Gelation and Chiral Aggregation of Alkylamides Derived from trans–1,2–Diaminocyclohexane*, Angew. Chem. Int. Ed. Engl. 1996, 35, No. 17, 1949–1951.
Toshimi Shimizu et al., *Stereochemical Effect of Even–Odd Connecting Links on Supramolecular Assemblies Made of 1–Glucosamide Bloaamphiphiles*, J. Am Chem. Soc. 1997, 119, 2812–2818.
P. Terech, "Low–Molecular Weight Organogelators," in *Specialist Surfactants*, ch. 8, pp. 208–268 (I.D. Robb, ed., 1997).
Kenji Hanabusa et al., *Terephthaloyl Derivatives as New Gelators; Excellent Gelation Ability and Remarkable Increase of Gel Strength by Adding Polymers*, 1999 Chemistry Letters 767.
Xuzhong Luo et al., *Self–assembled organogels formed by monoalkyl derivatives of oxamide*, 2000 Chem. Commun. 2091–92.
Kenji Hanabusa et al., *Easy Preparation and Gelation of New Gelator Based on L–Lysine*, 2000 Chem. Letters, 1070.
Bush Boake Allen, Inc., *Uniclear Formulations*, dated Oct. 13, 1998.
International Search Report in PCT/US 01/47459, dated Feb. 6, 2003.
International Search Report in PCT/US 01/47496, dated Feb. 26, 2003.
International Search Report in PCT/US 01/47499, dated Aug. 8, 2002.
International Search Report in PCT/US 01/47454, dated Aug. 29, 2002.
Partial International Search Report in PCT/US 01/47497, dated Aug. 30, 2002.
International Search Report in PCT/US01/47497, dated Dec. 2, 2002.
French Search Report in FR 9909176, (priority document), dated Mar. 23, 2000.
French Search Report in FR 9909177, (priority document).
French Search Report in FR 9916588, (priority document), dated Oct. 16, 2000.
French Search Report in FR 0001004, (priority document), dated Nov. 10, 2000.
French Search Report in FR 0000920 (priority document for PCT/FR01/00229, which is the priority document), dated Nov. 10, 2000.
International Search Report in PCT/FR01/00229 (the priority document), dated Jan. 24, 2000.
French Search Report in FR 0008084 (priority document), dated Mar. 28, 2001.
International Search Report in PCT/FR01/01958 (priority document), dated Oct. 26, 2001.

French Search Report in FR 0008913 (priority document), dated Mar. 28, 2001.
French Search Report in FR 0016161 (priority document), dated Sep. 6, 2001.
International Search Report in PCT/FR01/03940 (priority document for FR 0016161, which is the priority document), dated Mar. 13, 2002.
French Search Report in FR 0016163 (priority document), dated Aug. 1, 2001.
International Search Report in PCT/FR01/03945 (priority document for FR 0016163), dated May 31, 2002.
International Search Report in PCT/FR01/03939 (priority document for FR 0016164), dated Apr. 15, 2002.
French Search Report in FR 0016164 (priority document), dated Sep. 6, 2001.
International Search Report in PCT/FR01/03937 (priority document), dated Apr. 23, 2002.
French Search Report in FR 0016180 (priority document), dated Oct. 16, 2001.
International Search Report in PCT/FR01/03938 (priority document), dated Jun. 10, 2002.
International Search Report in PCT/IB01/02780, dated Apr. 10, 2002.
International Search Report in PCT/US00/33596, dated Aug. 8, 2001.
International Search Report in PCT/IB00/02000, dated Aug. 8, 2001.
International Search Report in PCT/IB01/02833, dated May 24, 2002.
International Search Report in PCT/IB00/02006, dated Aug. 8, 2001.
International Search Report in PCT/IB01/02840, dated Jun. 11, 2002.
International Search Report in PCT/IB01/02820, dated May 27, 2002.
International Search Report in PCT/IB00/02002, dated Sep. 4, 2001.
International Search Report in PCT/IB01/02786, dated Oct. 2, 2002.
French Search Report in FR 0100479, dated Sep. 17, 2001.
International Search Report in PCT/FR02/00129, dated Jun. 14, 2002.
French Search Report in FR 0100623, (priority document), dated Oct. 9, 2001.
International Search Report in PCT/FR02/00144, (priority document), dated Jun. 14, 2002.
French Search Report in FR 0100620, dated Nov. 6, 2001.
International Search Report in PCT/FR02/00194, dated May 12, 2002.
French Search Report in FR 0114529, dated Aug. 26, 2002.
French Search Report in FR 0114530, dated Aug. 26, 2002.
Patent Abstracts of Japan, vol. 006, No. 054, Apr. 9, 1982, JP 56 166276.
Patent Abstracts of Japan, vol. 1998, No. 14, Dec. 31, 1998, JP 10 259344.
Charles M. Hansen, "The Three Dimensional Solubility Parameter—Key to Paint Component Affinities: I. Solvents, Plasticizers, Polymers, and Resins," Journal of Paint Technology, vol. 39, No. 505, Feb. 1967, pp. 104–117.
Richard J. Lewis, Sr., "Ricinoleic Acid,"Hawley's Condensed Chemical Dictionary 927 (13th Ed. 1997).

* cited by examiner

NAIL POLISH COMPOSITION COMPRISING A POLYMER

This application claims the benefit of priority to French Application No. 01 00623, filed Jan. 17, 2001, and to U.S. Provisional Application No. 60/330,767, filed Oct. 30, 2001.

The present invention relates to a composition for caring for and/or treating and/or making up the nails of human beings, comprising a liquid organic phase including a volatile organic solvent, structured by a specific polymer. This composition is provided in particular in the form of a nail polish stick.

The makeup composition can also be applied to makeup accessories (support), such as false nails.

In nail polishes comprising an organic solvent medium, it is standard practice to thicken the organic phase with thickening agents.

The term "liquid organic phase" is understood to mean, within the meaning of the invention, an organic phase which is liquid at ambient temperature (25° C.) and which is composed of one or more organic compounds which are liquid at ambient temperature, also known as organic solvents or oils, generally compatible with one another. Thickened compositions make it possible to make it easier to take the product from its container without significant loss, to distribute the polish over the surface of the nail or alternatively to be able to use the polish in sufficient amounts to obtained the desired cosmetic effect. Furthermore, the thickening agent makes it possible to prevent the sedimentation during storage of the pigments often present in nail polishes.

The use is known, for thickening the compositions, of clays such as organomodified montmorillonites, such as disclosed in Application GB-A-2021411. In point of fact, clays opacify the composition and do not make possible the preparation of a translucent composition. Furthermore, clays are often formulated with an agent which promotes their swelling, such as citric acid or orthophosphoric acid, which can lead to instability of the composition.

Furthermore, nail polishes known to date are generally provided in the form of a fluid composition which is applied using a brush or alternatively a pen (see in particular U.S. Pat. No. 4,712,571).

The need thus remains for a composition which does not exhibit the above disadvantages. Furthermore, it is desirable to be able to have available a novel nail polish pharmaceutical dosage form different from the nail polishes known to date.

A subject matter of the invention is specifically a composition for caring for and/or making up and/or treating the nails which makes it possible to overcome the abovementioned disadvantages.

The applicant has found, surprisingly, that the use of specific polymers in combination with one or more volatile organic solvents makes it possible to obtain structured nail polishes, in particular a gel and more particularly a stick, the application of which to the nails results in a film having good cosmetic properties.

The invention applies not only to products for making up the nails but also to products for caring for and/or treating the nails.

More specifically, a subject matter of the invention is a structured nail polish composition comprising at least one liquid organic phase comprising at least one volatile organic solvent, the liquid organic phase being structured by at least one first polymer with a weight-average molecular mass of less than or equal to 100 000 comprising a) a polymer backbone having hydrocarbonaceous repeat units which are provided with at least one heteroatom and b) optionally functionalized pendent and/or end fatty chains which have from 6 to 120 carbon atoms and which are bonded to these hydrocarbonaceous units.

Another subject matter of the invention is a stick nail polish composition comprising an organic phase comprising a volatile organic solvent and a first polymer with a weight-average molecular mass of less than or equal to 100 000 comprising a) a polymer backbone having hydrocarbonaceous repeat units which are provided with at least one heteroatom and b) optionally functionalized pendent and/or end fatty chains which have from 6 to 120 carbon atoms and which are bonded to these hydrocarbonaceous units.

A further subject matter of the invention is a cosmetic process for caring for, making up or treating the nails, comprising the application, to the nails, of the composition, in particular cosmetic composition, as defined above.

Another subject matter of the invention is the use in a nail polish composition, for producing a stick, of a liquid organic phase comprising at least one volatile organic solvent and of a sufficient amount of a first polymer with a weight-average molecular mass of less than or equal to 100 000 comprising a) a polymer backbone having hydrocarbonaceous repeat units which are provided with at least one heteroatom and b) optionally functionalized pendent and/or end fatty chains which have from 6 to 120 carbon atoms and which are bonded to these hydrocarbonaceous units.

The nail polish composition of the invention can be provided in the form of a paste, solid, gel, cream or thickened liquid. It can be an oil-in-water or water-in-oil emulsion or a stiff or soft anhydrous gel. In particular, it is provided in the form cast as a stick or as a dish and more especially in the form of a stiff anhydrous gel, in particular an anhydrous stick. More especially, it is provided in the form of a stiff gel which can be translucent or transparent, the liquid organic phase forming the continuous phase.

The gelling of the solvent phase can be adjusted according to the nature of the heteroatom-comprising polymer used and can be such that a stiff structure in the form of a tube or stick is obtained.

The structuring polymer of the composition of the invention is a solid which is nondeformable at ambient temperature (25° C.).

The term "functionalized chains" is understood to mean, within the meaning of the invention, an alkyl chain comprising one or more functional or reactive groups chosen in particular from amide, hydroxyl, ether, oxyalkylene or polyoxyalkylene, halogen, ester, siloxane or polysiloxane groups, the halogen groups including fluorinated or perfluorinated groups. In addition, the hydrogen atoms of one or more fatty chains can be at least partially substituted by fluorine atoms.

According to the invention, these chains can be bonded directly to the polymer backbone or can be bonded via an ester functional group or a perfluorinated group.

The term "polymer" is understood to mean, within the meaning of the invention, a compound having at least 2 repeat units and preferably at least 3 repeat units which are identical.

The term "hydrocarbonaceous repeat units" is understood to mean, within the meaning of the invention, a unit comprising from 2 to 80 carbon atoms and preferably from 2 to 60 carbon atoms, carrying hydrogen atoms and optionally oxygen atoms, which can be linear, branched or cyclic and saturated or unsaturated. In addition, these units each comprise from one to several heteroatoms which are advantageously nonpendent heteroatoms and which are found in the polymer backbone. These heteroatoms are chosen from nitrogen, sulfur or phosphorus atoms and their combinations, optionally in combination with one or more oxygen atoms. Preferably, the units comprise at least one nitrogen atom, in particular one nonpendent nitrogen atom. Advantageously, these units additionally comprise a carbonyl group.

The heteroatom-comprising units are in particular amide units, forming a backbone of the polyamide type, or carbamate and/or urea units, forming a polyurethane, polyurea and/or polyurea/urethane backbone. These units are preferably amide units. Advantageously, the pendent chains are bonded directly to at least one of the heteroatoms of the polymer backbone. According to one embodiment, the first polymer comprises a polyamide backbone.

The first polymer can comprise, between the hydrocarbonaceous units, silicone units or oxyalkylenated units.

In addition, the first polymer of the composition of the invention advantageously comprises a total number of fatty chains which represents from 40 to 98% of the total number of the heteroatom-comprising units and of the fatty chains and better still from 50 to 95%. The nature and the proportion of the heteroatom-comprising units depends on the nature of the organic phase and is in particular similar to the polar nature of the organic phase. Thus, the greater the polarity of the heteroatom-comprising units and the greater their proportion in the first polymer, which corresponds to the presence of several heteroatoms, the greater the affinity of the first polymer for polar oils. On the other hand, the lower the polarity of the heteroatom-comprising units, indeed even when they are nonpolar, or the lower their proportion, the greater the affinity of the first polymer for nonpolar oils.

The first polymer is advantageously a polyamide. Consequently, another subject matter of the invention is a structured nail polish composition comprising at least one liquid organic phase comprising at least one volatile organic solvent, the liquid organic phase being structured by at least one polyamide with a weight-average molecular mass of less than or equal to 100 000 comprising a) a polymer backbone having amide repeat units and b), optionally, optionally functionalized pendent and/or end fatty chains which have from 6 to 120 carbon atoms and which are bonded to these amide units.

Another subject matter of the invention is a stick nail polish composition comprising a volatile organic solvent and a first polyamide polymer with a weight-average molecular mass of less than or equal to 100 000 comprising a) a polymer backbone having amide repeat units and b) optionally functionalized pendent and/or end fatty chains which have from 6 to 120 carbon atoms and which are bonded to these amide units.

Preferably, the pendent fatty chains are bonded to at least one of the nitrogen atoms of the amide units of the first polymer.

In particular, the fatty chains of this polyamide represent from 40 to 98% of the total number of the amide units and of the fatty chains and better still from 50 to 95%.

Advantageously, the first polymer and in particular the polyamide of the composition according to the invention exhibits a weight-average molecular mass of less than or equal to 100 000 (ranging in particular from 1 000 to 100 000), especially of less than 50 000 (ranging in particular from 1 000 to 50 000) and more especially ranging from 1 000 to 30 000, preferably from 2 000 to 20 000 and better still from 2 000 to 10 000.

Mention may be made, as preferred first polymers which can be used in the invention, of polyamides branched by pendent fatty chains and/or end fatty chains having from 6 to 120 carbon atoms and better still from 8 to 120 and in particular from 12 to 68 carbon atoms, each end fatty chain being bonded to the polyamide backbone via at least one bonding group, in particular an ester group. Preferably, these polymers comprise a fatty chain at each end of the polymer backbone and in particular of the polyamide backbone. Mention may be made, as other bonding group, of ether, amine, urea, urethane, thioether, thioester, thiourea or thiourethane groups.

These first polymers are preferably polymers resulting from a polycondensation between a dicarboxylic acid having at least 32 carbon atoms (having in particular from 32 to 44 carbon atoms) with a diamine having at least 2 carbon atoms (in particular from 2 to 36 carbon atoms). The diacid is preferably a dimer resulting from a fatty acid comprising ethylenic unsaturation having at least 16 carbon atoms, preferably from 16 to 24 carbon atoms, such as oleic acid, linoleic acid or linolenic acid. The diamine is preferably ethylenediamine, hexylenediamine or hexamethylenediamine. For polymers comprising one or 2 end carboxylic acid groups, it is advantageous to esterify them with a monoalcohol having at least 4 carbon atoms, preferably from 10 to 36 carbon atoms and better still from 12 to 24 and even better still from 16 to 24, for example 18 carbon atoms.

These polymers are more especially those disclosed in the document U.S. Pat. No. 5,783,657 of Union Camp. Each of these polymers satisfies in particular the following formula (I):

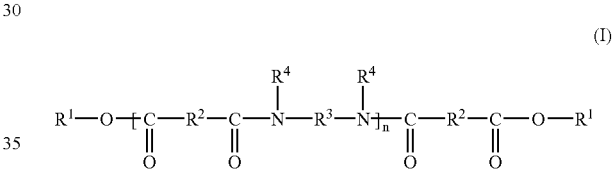

(I)

in which n denotes a whole number of amide units such that the number of ester groups represents from 10% to 50% of the total number of the ester and amide groups; $R^1$ is, in each case, independently an alkyl or alkenyl group having at least 4 carbon atoms and in particular from 4 to 24 carbon atoms; $R^2$ independently represents, in each case, a $C_4$ to $C_{42}$ hydrocarbonaceous group, provided that 50% of the $R^2$ groups represent a $C_{30}$ to $C_{42}$ hydrocarbonaceous group; $R^3$ independently represents, in each case, an organic group provided with at least 2 carbon atoms, with hydrogen atoms and optionally with one or more oxygen or nitrogen atoms; and $R^4$ independently represents, in each case, a hydrogen atom, a $C_1$ to $C_{10}$ alkyl group or a direct bond to $R^3$ or to another $R^4$, so that the nitrogen atom to which both $R^3$ and $R^4$ are bonded forms part of a heterocyclic structure defined by $R^4$—N—$R^3$, with at least 50% of the $R^4$ groups representing a hydrogen atom.

In the specific case of the formula (I), the optionally functionalized end fatty chains within the meaning of the invention are end chains bonded to the final heteroatom, in this instance nitrogen, of the polyamide backbone.

In particular, the ester groups of the formula (I), which form part of the end and/or pendent fatty chains within the meaning of the invention, represent from 15 to 40% of the total number of the ester and amide groups and better still from 20 to 35%. Furthermore, n advantageously represents an integer ranging from 1 to 5 and better still of greater than 2, in particular ranging from 3 to 5. Preferably, $R^1$ is a $C_{12}$ to $C_{22}$ alkyl group and preferably a $C_{16}$ to $C_{22}$ alkyl group. Advantageously, $R^2$ can be a $C_{10}$ to $C_{42}$ hydrocarbonaceous (alkylene) group. Preferably, at least 50% and better still at least 75% of the $R^2$ groups are groups having from 30 to 42 carbon atoms. The other $R^2$ groups are $C_4$ to $C_{19}$ and even $C_4$ to $C_{12}$ hydrogenated groups. Preferably, $R^3$ represents a $C_2$ to $C_{36}$ hydrocarbonaceous group or a polyoxyalkylenated group and $R^4$ represents a hydrogen atom. Preferably, $R^3$ represents a $C_2$ to $C_{12}$ hydrocarbonaceous group.

The hydrocarbonaceous groups can be linear, cyclic or branched and saturated or unsaturated groups. Furthermore, the alkyl and alkylene groups can be linear or branched and saturated or unsaturated groups.

The polymers of formula (I) are generally provided in the form of blends of polymers, it being possible for these blends to additionally comprise a synthetic product corresponding to a compound of formula (I) where n has the value 0, that is to say a diester.

Mention may be made, as examples of first polymers according to the invention, of the commercial products sold by Arizona Chemical under the names UNICLEAR 80 and UNICLEAR 100. They are sold respectively in the form of an 80% (as active material) gel in a mineral oil and of a 100% (as active material) gel. They have a softening point of 88 to 94° C. These commercial products are a blend of copolymers of a $C_{36}$ diacid condensed with ethylenediamine, with a weight-average molecular mass of approximately 6 000. The end ester groups result from esterification of the remaining acid endings with cetyl alcohol, stearyl alcohol or their mixtures (also known as cetearyl alcohol).

Mention may also be made, as first polymer which can be used in the invention, of polyamide resins resulting from the condensation of an aliphatic dicarboxylic acid and of a diamine (including compounds having more than 2 carbonyl groups and 2 amine groups), the carbonyl and amine groups of adjacent individual units being condensed via an amide bond. These polyamides are in particular those sold under the VERSAMID trademark by General Mills Inc. and Henkel Corp. (VERSAMID 930, 744 or 1655) or by Olin Mathieson Chemical Corp. under the ONAMID trademark, in particular ONAMID S or C. These resins have a weight-average molecular mass ranging from 6 000 to 9 000. For further information on these polyamides, reference may be made to the documents U.S. Pat No. 3,645,705 and U.S. Pat No. 3,148,125. More especially, VERSAMID 930 or 744 is used.

It is also possible to use the polyamides sold by Arizona Chemical under the UNI-REZ references (2658, 2931, 2970, 2621, 2613, 2624, 2665, 1554, 2623, 2662) and the product sold under the reference MACROMELT 6212 by Henkel. For further information on these polyamides, reference may be made to the document U.S. Pat. No. 5,500,209.

It is also possible to use polyamide resins resulting from vegetables, such as those disclosed in Patents U.S. Pat No. 5,783,657 and U.S. Pat No. 5,998,570, the contents of which are incorporated by way of reference in the present application.

The first polymer present in the composition according to the invention advantageously has a softening temperature of greater than 65° C. and which can range up to 190° C. Preferably, it exhibits a softening temperature ranging from 70 to 130° C. and better still from 80 to 105° C. The first polymer is in particular a nonwaxy polymer.

The first polymer according to the invention preferably corresponds to the formula (I) mentioned above. This first polymer exhibits, because of their fatty chain(s), good solubility in oils and thus results in macroscopically homogeneous compositions, even with a high level (at least 25%) of polymer, in contrast to polymers devoid of a fatty chain.

The first polymer can be present in the composition according to the invention in a content ranging from 0.1% to 60% by weight with respect to the total weight of the composition, preferably ranging from 0.5% to 30% by weight and better still ranging from 1% to 20% by weight.

The liquid organic phase of the composition according to the invention additionally comprises at least one volatile organic solvent, namely one or more volatile solvents.

The term "volatile organic solvent" is understood to mean, within the meaning of the invention, any nonaqueous medium capable of evaporating on contact with the skin or nails in less than one hour at ambient temperature and atmospheric pressure. The volatile solvent or solvents of the invention are organic solvents and in particular volatile cosmetic oils which are liquid at ambient temperature and which have a nonzero vapour pressure, at ambient temperature and atmospheric pressure, ranging in particular from $10^{-3}$ to 300 mm of Hg (0.013 Pa to 40 000 Pa) and preferably of greater than 0.1 mm of Hg (10 Pa) and better still of greater than 0.3 mm of Hg (30 Pa).

According to the invention, these volatile solvents in particular facilitate the application of the composition to the nails. These solvents can be hydrocarbonaceous solvents, silicone solvents optionally comprising pendent alkyl or alkoxy groups or alkyl or alkoxy groups at the end of the silicone chain, or a mixture of these solvents. Preferably, these solvents are not alcohols comprising at least 7 carbon atoms.

Advantageously, the liquid organic phase of the composition comprises at least one volatile organic solvent or a mixture of volatile organic solvents (within the meaning of the final mixture) exhibiting mean Hansen solubility parameters dD, dP and dH at 25° C. which satisfy the following conditions:

$$15 \leq dD \leq 19$$

$$dP \leq 10$$

$$dH \leq 10$$

Consequently, a subject matter of the invention is a cosmetic composition comprising an organic phase, a first polymer and a second additional film-forming polymer, the organic phase comprising at least one volatile organic solvent or a mixture of volatile organic solvents exhibiting mean Hansen solubility parameters dD, dP and dH at 25° C. which satisfy the conditions defined above.

Another subject matter of the invention is a nail polish composition comprising an organic phase, a first polymer and a second additional film-forming polymer, the organic phase comprising at least one volatile organic solvent or a mixture of volatile organic solvents exhibiting mean Hansen solubility parameters dD, dP and dH at 25° C. which satisfy the conditions defined above.

The definition of the solvents in the three-dimensional solubility space according to Hansen is described in the article by C. M. Hansen: "The three-dimensional solubility parameters", J. Paint Technol., 39, 105 (1967):

dD characterizes the London dispersion forces resulting from the formation of dipoles induced during molecular impacts;

dP characterizes the forces of Debye interaction between permanent dipoles and the forces of Keesom interactions between induced dipoles and permanent dipoles;

dH characterizes the forces of specific interactions (hydrogen bond, acid/base or donor/acceptor type and the like).

The parameters dD, dP and dH are expressed in $(J/cm^3)^{1/2}$.

Use is preferably made of an organic solvent such that $dP \leq 5$; $dH \leq 9$.

Advantageously, dD, dP and dH obey the relationship $$\sqrt{4(17-dD)^2+dP^2+dH^2} < L$$

L being equal to 10 $(J/cm^3)^{1/2}$ and better still 9 $(J/cm^3)^{1/2}$.

Mention may be made, as volatile organic solvent which can be used in the invention, of volatile hydrocarbonaceous oils having from 4 to 16 carbon atoms and their mixtures and in particular linear C6–C10 alkanes, such as n-hexane, n-heptane or n-octane, branched C8–C16 alkanes, such as C8–C16 isoalkanes (also known as isoparaffins), isododecane, isodecane, isohexadecane and, for example, the oils sold under the tradenames of ISOPARS or PERMETYLS, esters having from 4 to 8 carbon atoms, such as ethyl acetate, n-propyl acetate, isobutyl acetate or n-butyl acetate, branched C8–C16 esters, such as isohexyl neopentanoate, and their mixtures. Preferably, the volatile organic solvent is chosen from volatile hydrocarbonaceous oils having from 4 to 10 carbon atoms and their mixtures.

Mention may be made, as other volatile organic solvent which can be used in the invention, of linear or cyclic silicone oils having a viscosity at ambient temperature of less than 8 centistokes (8 $10^{-6}$ m$^2$/s) and having in particular from 2 to 7 silicon atoms, these silicones optionally comprising alkyl or alkoxy groups having from 1 to 10 carbon atoms. Mention may in particular be made, as volatile silicone oil which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and their mixtures.

Use may also be made of volatile fluorinated solvents.

Use is preferably made of a volatile organic solvent chosen from ethyl acetate, n-propyl acetate, isobutyl acetate, n-butyl acetate, heptane and their mixtures.

The volatile organic solvent can be present in the composition according to the invention in a content ranging from 20% to 98% by weight with respect to the total weight of the composition, preferably from 30% to 90% by weight and better still from 40% to 85% by weight.

The organic phase of the composition according to the invention can additionally comprise a nonvolatile oil which can be a polar oil or a nonpolar oil. The nonvolatile oil can be present in a content ranging from 0.01% to 10% by weight with respect to the total weight of the composition.

In particular, the polar oils can be chosen from:
hydrocarbonaceous vegetable oils with a high content of triglycerides composed of esters of fatty acids and of glycerol, the fatty acids of which can have various $C_4$ to $C_{24}$ chain lengths, it being possible for the chains to be linear or branched and saturated or unsaturated; these oils are in particular wheat germ, maize, sunflower, karite, castor, sweet almond, macadamia, apricot, soybean, cottonseed, alfalfa, poppy, pumpkinseed, sesame, cucumber, rapeseed, avocado, hazelnut, grape seed, blackcurrant seed, evening primrose, millet, barley, quinoa, olive, rye, safflower, candlenut, passionflower or musk rose oils; or triglycerides of caprylic/capric acids, such as those sold by Stearineries Dubois or those sold under the names MIGLYOL 810, 812 and 818 by Dynamit Nobel;

synthetic oils or synthetic esters of formula $R_5COOR_6$ in which $R_5$ represents the residue of a linear or branched fatty acid comprising from 1 to 40 carbon atoms and $R_6$ represents a hydrocarbonaceous chain, in particular a branched hydrocarbonaceous chain, comprising from 1 to 40 carbon atoms, provided that $R_5+R_6$ is $\geq 10$, such as, for example, purcellin oil (cetearyl octanoate), isononyl isononanoate, $C_{12}$ to $C_{15}$ alkyl benzoate, isopropyl myristate, 2-ethylhexyl palmitate, isostearate isostearate, or octanoates, decanoates or ricinoleates of alcohols or polyalcohols; hydroxylated esters, such as isostearyl lactate or diisostearyl malate; and pentaerythritol esters;

synthetic ethers having from 10 to 40 carbon atoms;

$C_8$ to $C_{26}$ fatty alcohols, such as oleyl alcohol;

their mixtures.

The nonpolar oils according to the invention are in particular silicone oils, such as linear or cyclic polydimethylsiloxanes (PDMSs) which are liquid at ambient temperature; polydimethylsiloxanes comprising pendent alkyl, alkoxy or phenyl groups and/or alkyl, alkoxy or phenyl groups at the end of the silicone chain, which groups have from 2 to 24 carbon atoms; phenylated silicones, such as phenyl trimethicones, phenyl dimethicones, phenyltrimethylsiloxydiphenyl-siloxanes, diphenyl dimethicones, diphenylmethyl-diphenyltrisiloxanes or (2-phenylethyl)trimethyl-siloxysilicates; linear or branched hydrocarbons of synthetic or mineral origin, such as liquid paraffins and its derivatives, petrolatum, liquid lanolin, polydecenes, hydrogenated polyisobutene, such as parleam, or squalane; and their mixtures.

Preferably, the oils are nonpolar oils and more especially an oil or a mixture of oils of the hydrocarbonaceous type of mineral or synthetic origin chosen in particular from hydrocarbons, especially alkanes, such as parleam oil, isoparaffins, such as isododecane and squalane, and their mixtures. Advantageously, these oils are used in combination with one or more phenylated silicone oils.

Preferably, use is made of a nonvolatile oil such that the mixture of volatile organic solvent and of nonvolatile oil exhibits mean Hansen solubility parameters dD, dP and dH at 25° C. which satisfy the conditions defined above.

According to a specific form of the invention, for a liquid organic phase structured by a polymer comprising a partially silicone-comprising backbone, this organic phase preferably comprises more than 40% of the total weight of the liquid organic phase and better still from 50 to 100% of silicone-comprising volatile organic solvent or of silicone-comprising nonvolatile oils with respect to the total weight of the liquid organic phase.

According to another specific form of the invention, for a liquid organic phase structured by a nonpolar polymer of the hydrocarbonaceous type, this organic phase advantageously comprises more than 40% by weight and better still from 50 to 100% of hydrocarbonaceous volatile organic solvent or of hydrocarbonaceous nonpolar nonvolatile oil with respect to the total weight of the liquid organic phase.

The total liquid organic phase represents, in practice, from 5 to 99% of the total weight of the composition, preferably from 20 to 75%.

According to the invention, the composition can be a stick having a hardness ranging from 30 to 300 g and better still from 30 to 250 g, in particular from 30 to 150 g, preferably from 30 to 120 g and, for example, from 30 to 50 g. The hardness of the composition according to the invention can be measured by the "cheesewire" method, which consists in cutting a stick of lipstick with a diameter of 12.7 mm and in measuring the hardness at 20° C. by means of a DFGHS 2 dynamometer from Indelco-Chatillon moving at a rate of 100 mm/minute. It is expressed as the shear force (expressed in grams) needed to cut a stick under these conditions.

The hardness of the composition can also be measured by the method of penetration of a probe into said composition and in particular using a texture analyzer (for example TA-XT2i from Rhéo) equipped with an ebonite cylinder with a height of 25 mm and a diameter of 8 mm. The hardness measurement is carried out at 20° C. at the center of five samples of said composition. The cylinder is introduced into each composition sample at a prerate of 2 mm/s, then at a rate of 0.5 mm/s and, finally, at a postrate of 2 mm/s, the total displacement being 1 mm. The value recorded of the hardness is that of the maximum peak. The measurement error is +/−50 g. According to this method, the hardness of the composition stick can range from 20 to 2 000 g, in particular from 20 to 1 500 g and better still from 20 to 900 g, for example from 50 to 600 g or even better still from 150 to 450 g.

The hardness of the composition according to the invention is such that the composition is advantageously self-supporting and can easily disintegrate to form a satisfactory layer on the nails. In addition, with this hardness, the composition of the invention possesses good impact strength.

The hardness of the composition according to the invention is such that the composition is self-supporting and can easily disintegrate to form a satisfactory layer on the nails. In addition, with this hardness, the composition of the invention possesses good impact strength.

Advantageously, the composition of the invention additionally comprises at least one subsidiary film-forming polymer other than said first polymer as described above.

The film-forming polymer can be chosen from cellulose polymers, such as nitrocellulose, cellulose acetate, cellulose acetate butyrate, cellulose acetate propionate or ethyl cellulose, or alternatively polyurethanes, acrylic polymers, vinyl polymers, polyvinylbutyrals, alkyd resins, resins resulting from aldehyde condensation products, such as aryl-sulfonamide-formaldehyde resins, for example toluene-sulfonamide-formaldehyde resin, or arylsulfonamide-epoxy resins.

Use may in particular be made, as film-forming polymer, of nitrocellulose RS ⅛ sec.; RS ¼ sec.; ½ sec.; RS 5 sec.; RS 15 sec.; RS 35 sec.; RS 75 sec.; RS 150 sec.; AS ¼ sec.; AS ½ sec.; SS ¼ sec.; SS ½ sec.; SS 5 sec.; sold in particular by Hercules; toluenesulfonamide-formaldehyde resin "KETJENTFLEX MS80" from Akzo or "Santolite MHP" or "Santolite MS80" from Faconnier or "Resimpol 80" from Pan Americana, alkyd resin "BECKOSOL ODE 230-70-E" from Dainippon, acrylic resin "ACRYLOID B66" from Röhm & Haas, or polyurethane resin "TRIXENE PR 4127" from Baxenden.

The subsidiary film-forming polymer can be present in the composition according to the invention in a content ranging from 0.1% to 60% by weight with respect to the total weight of the composition, preferably ranging from 2% to 40% by weight and better still from 5% to 25% by weight.

The composition of the invention can additionally comprise any additive conventionally used in the field under consideration chosen in particular from coloring materials, antioxidants, preservatives, fragrances, fillers, waxes, neutralizing agents, cosmetic or dermatological active principles, such as, for example, emollients, moisturizers or vitamins, spreading agents, sunscreens, and their mixtures. These additives can be present in the composition in a proportion of 0 to 20% (in particular of 0.01 to 20%) of the total weight of the composition and better still of 0.01 to 10%.

Of course, a person skilled in the art will take care to choose the optional additional additives and/or their amount so that the advantageous properties of the composition according to the invention are not, or not substantially, detrimentally affected by the envisaged addition.

Of course, the composition of the invention must be cosmetically or dermatologically acceptable, namely must comprise a nontoxic physiologically acceptable medium capable of being applied to the skin or superficial body growths of human beings. The term "cosmetically acceptable" is understood to mean, within the meaning of the invention, a composition with a pleasant appearance, a pleasant smell and a pleasant feel.

The coloring material according to the invention can be chosen from lipophilic dyes, pigments and pearlescent agents commonly used in cosmetic or dermatological compositions, and their mixtures. This coloring material is generally present in a proportion of 0.01 to 10% of the total weight of the composition, preferably of 0.1 to 8%, if it is present.

The fat-soluble dyes are, for example, Sudan red, DC Red 17, DC Green 6, β-carotene, soybean oil, Sudan brown, DC Yellow 11, DC Violet 2, DC Orange 5 or quinoline yellow. They can represent from 0.1 to 10% of the weight of the compositions and better still from 0.1 to 6%.

The pigments can be white or colored, inorganic and/or organic and coated or uncoated. Mention may be made, among inorganic pigments, of titanium dioxide, which is optionally surface treated, zirconium or cerium oxides and iron or chromium oxides, manganese violet, ultramarine blue, chromium hydrate and ferric blue. Mention may be made, among organic pigments, of carbon black, pigments of D & C type and lakes based on cochineal carmine or on barium, strontium, calcium or aluminum. The pigments can represent from 0.1 to 50% and better still from 2 to 30% of the total weight of the composition, if they are present.

The pearlescent pigments can be chosen from white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride. They can represent from 0.1 to 20% of the total weight of the composition and better still from 0.1 to 15%, if they are present.

The composition according to the invention can be manufactured by known processes used generally in the cosmetics or dermatological field.

The invention is illustrated in more detail in the following example. The percentages are given by weight.

EXAMPLE 1

A nail polish having the following composition was prepared:

| | |
|---|---|
| Resin formed from polyamide with end ester groups, sold under the name "Uniclear ® 100" by Arizona Chemical | 20 g |
| Nitrocellulose | 8 g |
| Pigments | 1 g |
| Butyl acetate | q.s. for 100 g |

The nail polish is provided in the form of a structured solid composition, such as a stick.

We claim:

1. A cosmetic process for making up the nails of human beings, comprising:
    applying to the nails of human beings an effective amount of a composition comprising:
        a liquid organic phase comprising at least one volatile organic solvent and at least one first polymer with a weight-average molecular weight of less than or equal to 100,000 comprising:
            a) a polymer backbone comprising hydrocarbon-based repeating units, said units comprising at least one hetero atom in said backbone, and
            b) at least one fatty chain containing from 6 to 120 carbon atoms and chosen from at least one pendent fatty chain and at least one terminal fatty chain, wherein the at least one fatty chain is linked to the hydrocarbon-based units and is optionally functionalized,
        wherein said at least one volatile organic solvent and said at least one first polymer are present in the composition in a combined amount effective to give a structured composition.

2. The cosmetic process according to claim 1, wherein the at least one first polymer is chosen from a polymer of formula (I) and mixtures thereof:

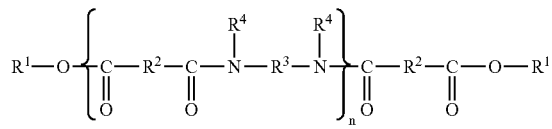

in which:
    n is an integer which represents the number of amide units such that the number of ester groups present in said at least one structuring polymer ranges from 10% to 50% of the total number of all said ester groups and all said amide groups comprised in said at least one structuring polymer;
    $R^1$, which are identical or different, are each chosen from alkyl groups comprising at least 4 carbon atoms and alkenyl groups comprising at least 4 carbon atoms;
    $R^2$, which are identical or different, are each chosen from $C_4$ to $C_{42}$ hydrocarbon-based groups with the proviso that at least 50% of $R^2$ are chosen from $C_{30}$ to $C_{42}$ hydrocarbon-based groups;
    $R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and
    $R^4$, which are identical or different, are each chosen from hydrogen atoms, $C_1$ to $C_{10}$ alkyl groups and a direct bond to group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

3. The cosmetic process according to claim 2, wherein the at least one first polymer is chosen from ethylenediamine/stearyl dimer tallate copolymer.

4. The cosmetic process according to claim 1, wherein said organic phase comprises at least one volatile organic solvent exhibiting mean Hansen solubility parameters dD, dP and dH at 25° C., wherein dD, dP and dH satisfy the following conditions:

$$15\ (J/cm^3)^{1/2} \leq dD \leq 19\ (J/cm^3)^{1/2}$$

$$dP \leq 10\ (J/cm^3)^{1/2};\ \text{and}$$

$$dH \leq 10\ (J/cm^3)^{1/2}.$$

5. The cosmetic process according to claim 4, wherein $dP \leq 5\ (J/cm^3)^{1/2}$.

6. The cosmetic process according to claim 4, wherein $dH \leq 9\ (J/cm^3)^{1/2}$.

7. The cosmetic process according to claim 4, wherein dD, dP and dH obey the relationship $$\sqrt{4(17-dD)^2 + dP^2} < L$$

wherein L is equal to 10 $(J/cm^3)^{1/2}$.

8. The cosmetic process according to claim 7, wherein L is equal to 9 $(J/cm^3)^{1/2}$.

9. The cosmetic process according to claim 1, wherein the composition further comprises at least one second film-forming polymer.

10. The cosmetic process according to claim 9, wherein the at least one second film-forming polymer is chosen from cellulose polymers, polyurethanes, acrylic polymers, vinyl polymers, polyvinylbutyrals, alkyd resins, resins resulting from aldehyde condensation products, and arylsulfonamide-epoxy resins.

11. The cosmetic process according to claim 1, wherein the at least one volatile organic solvent is chosen from esters having from 4 to 8 carbon atoms and linear alkanes having from 6 to 10 carbon atoms.

12. The cosmetic process according to claim 1, wherein the at least one volatile organic solvent is chosen from ethyl acetate, n-propyl acetate, isobutyl acetate, n-butyl acetate, and heptane.

13. The cosmetic process according to claim 1, wherein the at least one volatile organic solvent is chosen from branched $C_8$–$C_{16}$ alkanes, and branched $C_8$–$C_{16}$ esters.

14. The cosmetic process according to claim 1, wherein the volatile organic solvent is chosen from $C_8$–$C_{16}$ isoparaffins, and isododecane.

15. The cosmetic process according to claim 1, wherein the liquid organic phase additionally comprises at least one nonvolatile oil.

16. The composition according to claim 1, wherein the composition further comprises at least one additive chosen from coloring materials, antioxidants, preservatives, fragrances, fillers, waxes, neutralizing agents, cosmetic or dermatological active principles, dispersing agents, spreading agents, and sunscreens.

17. The cosmetic process according to claim 2, wherein the at least one first polymer is chosen from ethylenediamine/stearyl dimer dilinoleate copolymer.

* * * * *

UNITED STATES PATENT AND TRADEMARK OFFICE
CERTIFICATE OF CORRECTION

PATENT NO. : 7,025,953 B2　　　　　　　　　　　　　　　　　　　　　　　　Page 1 of 1
APPLICATION NO. : 10/046568
DATED : April 11, 2006
INVENTOR(S) : Xavier Blin et al.

It is certified that error appears in the above-identified patent and that said Letters Patent is hereby corrected as shown below:

Claim 7, column 12, line 21, " $\sqrt{4(17-dD)^2 + dP^2}$ <L" should read

-- $\sqrt{4(17-dD)^2 + dP^2 + dH^2}$ <L --

Signed and Sealed this

Tenth Day of October, 2006

JON W. DUDAS
*Director of the United States Patent and Trademark Office*